(12) United States Patent
Caulkett

(10) Patent No.: US 6,723,723 B1
(45) Date of Patent: Apr. 20, 2004

(54) HETEROCYCLIC DERIVATIVES AS INHIBITORS OF FACTOR XA

(75) Inventor: Peter W. R. Caulkett, Macclesfield (GB)

(73) Assignee: AstraZeneca, Sodertalje (SE)

( * ) Notice: Subject to any disclaimer, the term of this patent is extended or adjusted under 35 U.S.C. 154(b) by 0 days.

(21) Appl. No.: 09/913,071

(22) PCT Filed: Feb. 8, 2000

(86) PCT No.: PCT/GB00/00354

§ 371 (c)(1),
(2), (4) Date: Nov. 15, 2001

(87) PCT Pub. No.: WO00/47573

PCT Pub. Date: Aug. 17, 2000

(30) Foreign Application Priority Data

Feb. 11, 1999 (GB) ................................. 9902989

(51) Int. Cl.⁷ ..................... C07D 401/14; A61K 31/395
(52) U.S. Cl. ................................. 514/253.09; 544/364
(58) Field of Search ....................... 544/364; 514/253.09

(56) References Cited

U.S. PATENT DOCUMENTS

| | | |
|---|---|---|
| 4,167,567 A | 9/1979 | McCall |
| 4,231,938 A | 11/1980 | Monaghan et al. |
| 4,537,896 A | 8/1985 | Claeson et al. |
| 4,564,610 A | 1/1986 | Rahtz et al. |
| 4,629,728 A | 12/1986 | Regnier et al. |
| 4,788,196 A | 11/1988 | Cross et al. |
| 4,806,536 A | 2/1989 | Cross et al. |
| 4,835,165 A | 5/1989 | Cross et al. |
| 4,840,963 A | 6/1989 | Shepard et al. |
| 4,968,704 A | 11/1990 | Cross et al. |
| 5,032,604 A | 7/1991 | Baldwin et al. |
| 5,037,824 A | 8/1991 | Takasugi et al. ......... 514/227.8 |
| 5,138,058 A | 8/1992 | Geisen et al. |
| 5,254,563 A | 10/1993 | Huth et al. |
| 5,332,822 A | 7/1994 | Misra |
| 5,364,865 A | 11/1994 | Diana |
| 5,371,091 A | 12/1994 | Misra et al. |
| 5,391,556 A | 2/1995 | Heckel et al. |
| 5,411,971 A | 5/1995 | Edmonds-Alt et al. |
| 5,541,330 A | 7/1996 | Wear et al. .................. 546/257 |
| 5,556,977 A | 9/1996 | Wayne et al. |
| 5,563,141 A | 10/1996 | Wayne et al. |
| 5,580,881 A | 12/1996 | Binet et al. |
| 5,606,065 A | 2/1997 | Emonds-Alt et al. |
| 5,681,954 A | 10/1997 | Yamamoto et al. |
| 5,795,893 A | 8/1998 | Bondinell et al. |
| 5,856,326 A | 1/1999 | Anthony et al. |
| 5,883,096 A | 3/1999 | Lowe et al. |
| 5,908,843 A | 6/1999 | Gante et al. |
| 5,965,559 A | 10/1999 | Faull et al. |
| 6,022,869 A | 2/2000 | Faull et al. |
| 6,037,343 A | 3/2000 | Ali |
| 6,090,813 A | 7/2000 | Waterson et al. |
| 6,093,718 A | 7/2000 | Waterson et al. |
| 6,225,309 B1 | 5/2001 | Faull et al. |
| 6,300,330 B1 | 10/2001 | Stocker et al. |
| 6,313,127 B1 | 11/2001 | Waterson et al. |
| 6,335,341 B1 | 1/2002 | Johnson |
| 6,391,880 B1 | 5/2002 | Foubister et al. |
| 6,395,731 B1 | 5/2002 | Thorsten et al. |
| 6,440,972 B1 | 8/2002 | Brown |
| 6,458,793 B1 | 10/2002 | Warner |

FOREIGN PATENT DOCUMENTS

| | | |
|---|---|---|
| AU | 10177/92 | 7/1992 |
| DE | 39 05 364 A1 | 8/1990 |
| DE | 39 43 225 A | 6/1991 |
| DE | 42 43 858 A1 | 6/1994 |
| DE | 43 06 506 A1 | 9/1994 |
| EP | 0 097 630 A2 | 1/1984 |
| EP | 0 232 740 A1 | 8/1987 |
| EP | 0 233 051 | 8/1987 |
| EP | 0 244 115 | 11/1987 |
| EP | 0 324 421 A2 | 7/1989 |
| EP | 0 308 337 | 9/1989 |
| EP | 0 352 946 A1 | 1/1990 |
| EP | 0 359 389 | 3/1990 |

(List continued on next page.)

OTHER PUBLICATIONS

Nowak et al., Chemical Abstracts, vol. 131:337034, 1999.
Prasad et al., "Antiamoebic Action of Drugs and Synthetic Compounds Against Trophozoites of Entamoeba Histoltica Under Axenic and Polyxenic Culture Conditions and in the Infected Rat Caecum", Curr. Sci., Aug. 1984, pp. 778–781.
Ratouis et al., "Synthetic and Pharmacological Study of New Piperazine Derivatives, II. Phenethylpiperazines", J. Med. Chem., Jan. 1965, pp. 104–107.
Sartori et al., "Synthesis and analgesic activities of urea derivatives of α–amino–N–pyridyl benzene propanamide", Eur J. Med Chem (1994), pp. 431–439.

(List continued on next page.)

*Primary Examiner*—Deepak Rao
(74) *Attorney, Agent, or Firm*—Morgan, Lewis & Bockius LLP

(57) ABSTRACT

The invention relates to heterocyclic derivatives, or pharmaceutically-acceptable salts thereof, of formula (I) wherein: A is an optionally substituted 5- or 6-membered monocyclic aromatic ring containing 1, 2 or 3 ring heteroatoms selected from oxygen, nitrogen and sulphur atoms; which possess antithrombotic and anticoagulant properties and are accordingly useful in methods of treatment of humans or animals. The invention also relates to processes for the preparation of the heterocyclic derivatives, to phaautical compositions containing them and to their use in the manufacture of medicaments for use in the production of an antithrombotic or anticoagulant effect.

(I)

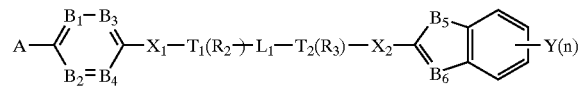

13 Claims, No Drawings

FOREIGN PATENT DOCUMENTS

| | | |
|---|---|---|
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 555 824 A1 | 8/1993 |
| EP | 0 576 941 A1 | 1/1994 |
| EP | 0 608 759 A2 | 8/1994 |
| FR | 2 697 252 A1 | 4/1994 |
| GB | 1 449 100 | 7/1976 |
| IE | 920095 | 7/1992 |
| WO | WO 92/08709 | 5/1992 |
| WO | WO 92/18478 | 10/1992 |
| WO | WO 93/06085 | 4/1993 |
| WO | WO 94/18185 | 8/1994 |
| WO | WO 94/20467 | 9/1994 |
| WO | WO 94/20468 | 9/1994 |
| WO | WO 94/22835 | 10/1994 |
| WO | WO 96/05189 | 2/1996 |
| WO | WO 96/10022 | 4/1996 |
| WO | WO 96/26196 | 8/1996 |
| WO | WO 96/30343 | 10/1996 |
| WO | WO 96/33171 | 10/1996 |
| WO | WO 97/06802 | 2/1997 |
| WO | WO 97/28128 | 8/1997 |
| WO | WO 97/28129 | 8/1997 |
| WO | WO 97/29104 | 8/1997 |
| WO | WO 97/30971 | 8/1997 |
| WO | WO 98/06705 | 2/1998 |
| WO | WO 98 21188 | 5/1998 |
| WO | WO 99 06371 | 8/1999 |
| WO | WO 99 57113 | 11/1999 |

OTHER PUBLICATIONS

Sato et al., "Synthetic Studies on Cardiovascular Agents. III. Synthetsis of Pyrano–[2,3–c]pyrazoline Derivatives", Yakugaku Zasshi, vol. 98(3), 1978, pp. 335–348.

Saxena et al., "Quantitative Structure Activity Relationship in 3–4 Disubstituted Pyridines & 1–(3"–Amino–4"pyridyl)–4–arylpiperazines", Indian J. Chem., vol. 19B, Oct., 1980, pp. 873–878.

Sherman, "Heparin and heparinoids in stroke", PubMed Abstract—Neurology, 51(3 Suppl): S56–8, Sep. 1998.

Smith et al., "Fibrin, Red Cell and Platelet Interactions in an Experimental Model of Thrombosis", Br. J. Pharmac., vol. 77, pp. 29–38 (1982).

Sundberg et al., "Synthesis with N–Protected–2–Lithioindoles", J. Org. Chem., 1973, 38(19) 3324–3330.

Szmant et al., "Concerning the Variable Character of the Sulfone Group", J. Amer. Chem. Soc., vol. 78, pp. 3400–3403 (1956).

Boissier et al., "Synthesis and Pharmacological Study of New Piperazine Derivatives. !. Benzylpiperazines", J. Med. Chem., Sep. 1963, pp. 541–544.

Bowers Nemia et al., "Synthetic Routes to 3–Pyrrolidinol", Synth. Comm. 13(13):1117–1123 (1983).

Brown et al., "A Novel Series of 4–Piperidinopyridine and 4–Piperidinopyrimidine Inhibitors of 2,3–Oxidosqualene Cyclase–Lanosterol Synthase", J. Med. Chem, 2000, vol. 43, pp. 4964–4972.

Budavari: Merck Index, vol. 11 ED., 1989, See Monograph numbers 804 and 2807.

Cattel et al., "Drug design based on biosynthetic studies: synthesis, biological activity, and kinetics of new inhibitors of 2,3–oxidosqualene cyclase and squalene epoxidase", Steroids, vol. 53, No. 3–5, 1989, pp. 363–391, XP000611661.

Caulkett et al., Chemical Abstracts. vol. 131:322629.

Chambers et al., "Preparation of arylpryridine compounds for treating leukotriene–related diseases", Chemical Abstracts, Abstract No. 139113, vol. 119 (1993).

Conway et al., "Approaches to the Generation of 2,3–Indolyne", Heterocycles, 1992, 34(11) pp. 2095–2108.

Cross et al., "Preparation of N–[(heterocyclicylmethoxy)phenyl] sulfamides and analogs as antiarrhythmics", Chemical Abstracts, Abstract No. 231211, vol. 113 (1989).

Deratani et al., "Synthesis of new dialkylaminopyridine acylation catalysts and their attachment to insoluble polymer supports", Polymer, Apr. 1987, pp. 825–830.

Hibino et al., "N–Phenysulfonylindole derivatives", Chemical Abstracts, 118:147461, Apr., 1993.

Jain et al., "Compounds Acting on the Central Nervous System, VII. Studies in 1–Pyridyl–1–substituted Piperazines. A New Class of Anticonvulsants", J. Med. Chem., Sep. 1967, pp. 812–818.

Jucker, "Über C–substituierte Piperazinderativate", Helv. Chim. Acta., 45:2383–2042 (1962).

Kataoka et al., Chemical Abstracts, vol. 123, No. 14, Oct. 2, 1995, Columbus, Ohio, U.S.; Abstract No. 179521d, "Homopiperazines as cell migration inhibitors", XP00201582, see abstract & JP 95 145060 A (Tejin Ltd).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. 1)Reactions of Acetoacetamide and β–Aminocrotonamide and β–Diketone, β–Ketoaldehyde and Related Compounds", Chem. Pharm. Bull., 24(2):303–309 (1976).

Kawasaki et al., (PubMed Abstract—Nippon Yakurigaku Zasshi, 116(5), 275–282, Nov., 2000.

Kettner et al., "The Selective Inhibition of Thrombin by Peptides of Boroarginine", The Journal of Biological Chemistry, vol. 265, No. 30, pp. 18289–18297 (1990).

Kobayashi et al., Chemical Abstracts, vol. 130:296694, 1999.

Kobayashi et al., Chemical Abstracts, vol. 132:194391, 2000.

Kunitada et al., "Factor Xa Inhibitors" Current Pharmaceutical Design. vol. 2, No. 5, Oct. 1996, pp. 531–542.

Lutz et al., Chem. Abstract 125:300774, 1996.

Mitsunobu et al., "Preparation of Carboxylic Esters and Phosphoric Esters by the Activation of Alcohols", Bull. Chem. Soc. Jpn., 44(12):3427–3430 (1971).

Tabacik et al., "Squalene expoxidase, oxido–squalene cyclase and cholesterol biosynthesis in normal and tumoral mucosa of the human gastrointestinal tract. Evidence of post–HMGACoA regulation", Biochim. Biophys. Acta, vol. 666, No. 3, 1982, pp. 433–441, XP000610864.

Take et al., Chemical Abstracts, vol. 133:58814, 2000.

Tawada et al., Chemical Abstracts, vol. 130:38404, 1999.

Tawada et al., Chemical Abstracts, vol. 131:170361, 1999.

Vigroux et al., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Prodrugs of Acetaminophen", J. Med. Chem., vol. 38, pp. 3983–3994 (1995).

Vogel et al., "Cpmparison of Two Experimental Thrombosis Models In Rats Effects of Four Glycosaminoglycans", Thrombosis Research, vol. 54, No. 5, pp. 399–410 (1989).

Von G. Krüger, et al., "(Thomae et al.) Arzneim.–Fosch., Synthesen von N–Benzyl–aminocarbonsäuren und thren Derivaten", (Synthesis and N–benzylaminocarboxylic acids and their derivatives), vol. 23(2a), pp. 290–295.

Wallis, "Inhibitors of Coagulation Factor Xa: From Macromolecular Beginnings to Small Molecules", Current Opinion in Therapeutic Patients, Aug., 1993, pp. 1173–1179.

Yokoyama et al., "Palladium–catalyzed cross–coupling reaction: direct allylation of aryl bromides with allyl acetate", Tetrahedron Letters, vol. 26, No. 52, 195, pp. 6457–6460, XP002081581 Oxford GB, pp. 6458–64569: compound 7.

Yokoyama et al., "Palladium–catalyzed cross–coupling reaction: direct allylation of aryl bromides with allyl acetate", Tetrahedron Letters, vol. 26, No. 52, 195, pp. 6457–6460, XP002081581 Oxford GB, pp. 6458–64569: compound 7, 1985.

Zaoral et al., "Amino acids and peptides. LIX. Synthesis and some biological properites of L–DABB–vasopressin", Collec. Czech. Chem. Commun., vol. 31, 1966, pp. 90–95, XP002081879, see compound 11, p. 95.

Zhu et al., Factor Xa Inhibitors: Recent Advances In Acticoagulant Agents, Ann. Report Med. Chem., 35, pp. 83–102, 2000.

Zurita et al., Chem. Abstract 122:155055, 1995.

HETEROCYCLIC DERIVATIVES AS INHIBITORS OF FACTOR XA

This application is the National Phase of International Application PCT/GB00/00354 filed Feb. 8, 2000 which designated the U.S. and that International Application.

The invention relates to heterocyclic derivatives, or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

Accordingly in one aspect the present invention provides compounds of the formula

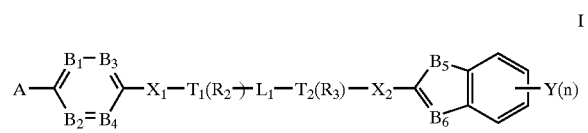

I wherein:
A is an optionally substituted 5- or 6-membered monocyclic aromatic ring containing 1, 2 or 3 ring heteroatoms selected from oxygen, nifrogen and sulphur atoms;

$B_1$, $B_2$, $B_3$ and $B_4$ are independently CH or a nitrogen atom, wherein the ring formed from $B_1$, $B_2$, $B_3$ and $B_4$ may optionally be substituted; with the proviso that at least one of $B_1$, $B_2$, $B_3$ and $B_4$ is nitrogen;

$T_1$ is CH or N;

$T_2$ is CH or N; with the proviso that at least one of $T_1$ and $T_2$ is N;

$X_1$ is SO, $SO_2$, $C(R_4)_2$ or CO when $T_1$ is CH or N; or in addition $X_1$ is O or S when $T_1$ is CH;

and wherein each $R_4$ is independently hydrogen or (1–4C)alkyl;

$L_1$ is (1–4C)alkylene or (1–3 C)alkylenecarbonyl;

$R_2$ is hydrogen or (1–4C)alkyl;

$R_3$ is hydrogen or (1–4C)alkyl;

or $R_2$ and $R_3$ are joined to form a (1–4C)alkylene or —$CH_2CO$— group; wherein the ring formed by $T_1$, $R_2$, $R_3$, $T_2$ and $L_1$ is optionally substituted;

$X_2$ is $S(O)_y$ wherein y is one or two, $C(R^5)_2$ or CO; and each $R^5$ is independently hydrogen or (1–4C)alkyl;

Y is selected from hydrogen, halo, trifluromethyl, trifluoromethoxy, cyano, hydroxy, amino, nitro, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl and N,N-di-(1–4C)alkylcarbamoyl-(1–4C)alkyl;

n is 1 or 2; and $B_5$ and $B_6$ is selected from N or CH; with the proviso that at least one of $B_5$ and $B_6$ is N;

and pharmaceutically acceptable salts thereof.

In this specification the term "alkyl" includes both straight and branched chain alkyl groups but references to individual alkyl groups such as "propyl" are specific for the straight chain version only. An analogous convention applies to other generic terms.

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is fuirther to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

Preferably A is a pyridyl, pyrimidinyl or pyridazinyl ring for example 4-pyridyl, 2-pyridyl, 4-pyridazinyl, 3-pyrimidinyl, 4-pyrimidinyl or 3-pyridyl. Of these 4-pyrimidinyl, 4-pyradaziiiyl and 4-pyridyl are preferred, with 4-pyrimidinyl and 4-pyridyl most preferred.

In one aspect A is unsubstituted. In another aspect A is substituted by one, two or three atoms or groups selected from halo (for example fluoro, chloro or bromo), trifluoromethyl, cyano, amino, oxo, hydroxy, nitro, (1–4C) alkyl (for example methyl or ethyl), (1–4C)alkoxy (for example methoxy or ethoxy), (1–4C)alkylamino (for example methylamino or ethylamino) or di-(1–4C) alkylamino (for example dimethylamino or diethylamino). For the avoidance of doubt substituents may also be on any heteroatom.

Preferably the ring formed by $B_1$, $B_2$, $B_3$ and $B_4$ is a pyridinediyl, wherein $B_1$, or $B_3$ is a nitrogen atom, pyrimidinediyl, wherein $B_1$ and $B_2$ or $B_3$ and $B_4$ are nitrogen atoms, pyridazinediyl, wherein $B_1$, $B_3$ and $B_4$ or $B_1$, $B_2$ and $B_3$ are nitrogen atoms. Of these pyridinediyl and pyrimidinediyl are preferred, and pyridinediyl is most preferred.

In one aspect the ring containing $B_1$, $B_2$, $B_3$ and $B_4$ is unsubstituted. In another aspect the ring containing $B_1$, $B_2$, $B_3$ and $B_4$ is substituted by one or two substituents selected from hydroxy, carboxy, (1–4C)alkoxycarbonyl or one of the following;

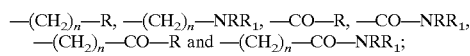

wherein n is 1 or 2;

R and $R_1$ are independently selected from hydrogen, (1–4C)alkyl, (2–4C)alkenyl, (2–4C)alkynyl, hydroxy (1–4C)alkyl, carboxy(1–4C)alkyl and (1–4C) alkoxycarbonyl-(1–4C)alkyl or where possible R and $R_1$ may together form a 5- or 6-membered optionally substituted heterocyclic ring which may include in addition to the nitrogen atom to which R and $R_1$ are attached 1 or 2 additional heteroatoms selected from nitrogen, oxygen and sulphur.

In a particular aspect the heterocylcic rings formed by R and $R_1$ are preferably selected from pyrrolidin-1-yl, imidazolin-1-yl, piperidin-lyl, piperazin-1-yl, 4-morpholino and 4-thiomorpholino. In a particular aspect the heterocyclic ring formed by R and $R_1$ may be unsubstituted. In an alternative aspect the ring formed by R and $R_1$ is substituted by 1 or 2 substituents selected from oxo, hydroxy and carboxy.

In a particular aspect, when $T_1$ is CH or N, $X_1$ is CO, $SO_2$, or $CH_2$ or, when $T_1$ is CH, $X_1$ in addition is O or S. Preferably $X_1$ is CO.

$T_1$ is CH or N and $T_2$ is CH or N with the proviso that at least one of $T_1$ and $T_2$ is N. For the avoidance of doubt $T_1$ is directly attached to the groups $X_1$ and $L_1$ and $T_2$ is directly attached to the groups $L_1$ and $X_2$.

$L_1$ is (1–4C)alkylene for example methylene. ethylene or propylene or is $C_{1-3}$alkylenecarbonyl for example methylenecarbonyl (—$CH_2CO$—), preferably $L_1$ is ethylene.

In one aspect $R_2$ is hydrogen or (1–4C)alkyl for example methyl or ethyl. In one aspect $R_3$ is hydrogen or $C_{1-4}$alkyl for example methyl or ethyl.

In a preferred aspect $R_2$ and $R_3$ are joined to form a (1–4C)alkylene group, for example a methylene, ethylene or propylene group, or a methylenecarbonyl (—$CH_2CO$—) group, preferably ethylene.

In a particular aspect $R_2$ and $R_3$ are joined to form, together with $T_1$, $T_2$ and $L_1$, a heterocyclic ring wherein at least one of $T_1$ and $T_2$ is N. Examples of such heterocyclic rings are piperazine (wherein $T_1$ and $T_2$ are both N), piperidine (wherein either $T_1$ or $T_2$ is N and the other is CH) and pyrrolidine (wherein either $T_1$ or $T_2$ is N and other is CH).

In one aspect the heterocyclic ring formed by $T_1$, $T_2$, $L_1$, $R_2$ and $R_3$ is unsubstituted. In another aspect this ring is substituted by one or two substituents selected from hydroxy, oxo, carboxy, (1–4C)alkoxycarbonyl or one of the following;

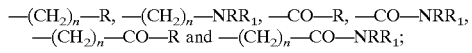

wherein n is 1 or 2;

R and $R_1$ are independently selected from hydrogen, (1–4C)alkyl, (2–4C)alkenyl, (2–4C)alkynyl, hydroxy (1–4C)alkyl, carboxy(1–4C)alkyl and (1–4C) alkoxycarbonyl-(1–4C)alkyl or where possible R and $R_1$ may together form a 5- or 6-membered optionally substituted heterocyclic ring which may include in addition to the nitrogen atom to which R and $R_1$ are attached 1 or 2 additional heteroatoms selected from nitrogen, oxygen and sulphur.

In a particular aspect the heterocylcic rings formed by R and $R_1$ are preferably selected from pyrrolidin-1-yl, imidazolin-1-yl, piperidin-1-yl, piperazin-1-yl, 4-morpholino and 4-thiomorpholino. In a particular aspect the heterocyclic ring formed by R and $R_1$ may be unsubstituted. In an alternative aspect the ring formed by R and $R_1$ is substituted by 1 or 2 substituents selected from oxo, hydroxy, carboxy and (1–4C)alkyl, preferably oxo, hydroxy, and carboxy.

In a particular aspect $X_2$ is $SO_2$, $CH_2$ or CO. Preferably $X_2$ is $SO_2$.

In a preferred aspect Y is selected from from hydrogen, halo (bromo or chloro), trifluromethyl, trifluoromethoxy, cyano, hydroxy, amino, nitro, carboxy, carbamoyl. (1–4C) alkyl, (2–4C)alkenyl, (2–4C)alkynyl, (1–4C)alkoxy, (2–4C) alkenyloxy, (2–4C)alkynyloxy, (1–4C)alkylthio, (1–4C) alkylsulphinyl, (1–4C)alkylsulphonyl, (1–4C)alkylamino, di-(1–4C)alkylamino and (1–4C)alkoxycarbonyl.

Suitable values for substituents Y are:

for halo: fluoro, chloro, bromo;

for (1–4C)alkyl: methyl, ethyl, propyl, butyl;

for (1–4C)alkoxy: methoxy, ethoxy;

for (1–4C)alkylamino: methylamino, ethylamino;

for di-(1–4C)alkylamino: dimethylamino, diethylamino;

for (2–4C)alkenyl: vinyl and allyl;

for (2–4C)alkynyl: ethynyl and prop-2-ynyl;

for (2–4C)alkenyloxy: vinyloxy and allyloxy;

for (2–4C)alkynyloxy: ethynyloxy and prop-2-ynyloxy;

for (1–4C)alkylthio: methylthio, ethylthio and propylthio;

for (1–4C)alkylsulphinyl: methylsulphinyl, ethylsulphinyl and propylsulphinyl;

for (1–4C)alkylsulphonyl: methylsulphonyl, ethylsulphonyl and propylsulphonyl;

for (2–4C)alkanoylamino: acetamido, propionamido and butyramido;

for (1–4C)alkoxycarbonyl: methoxycarbonyl, ethoxycarbonyl, propoxycarbonyl and tert-butoxycarbonyl;

for N-(1–4C)alkylcarbamoyl: N-methylcarbamoyl, N-ethylcarbamoyl and N-propylcarbamoyl;

for N-di-[(1–4C)alkyl]carbamoyl: N,N-dimethylcarbamoyl, N-ethyl-N-methylcarbamoyl and N,N,-diethylcarbamoyl;

for (2–4C)alkanoyl: acetyl, propionyl and butyryl;

for hydroxy-(1–4C)alkyl: hydroxymethyl, 1-hydroxyethyl, 2-hydroxyethyl and 3-hydroxypropyl;

for(1–4C)alkoxy-(1–4C)alkyl: methoxymethyl, ethoxymethyl, 1-methoxymethyl, 2-methoxyethyl, 2-ethoxyethyl and 3-methoxypropyl;

for carboxy-(1–4C)alkyl: carboxymethyl, 1-carboxyethyl, 2-carboxyethyl and 3-carboxypropyl;

for (1–4C)alkoxycarbonyl-(1–4C)alkyl: methoxycarbonylmethyl, ethoxycarbonylmethyl, tert-butoxy-carbonylmethyl, 1-methoxycarbonylethyl, 1-ethoxycarbonylethyl, 2-methoxycarbonylethy, 2-ethoxycarbonylethyl, 3-methoxycarbonylpropyl and 3-ethoxycarbonylpropyl;

for carbamoyl-(1–4C)alkyl: carbamoylmethyl, 1-carbamoylethyl, 2-carbamoylethyl and 3-carbamoylpropyl;

for N-(1–4C)alkylcarbamoyl-(1–4C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1–4C)alkyl]carbamoyl-(1–4C)alkyl:N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbanoyl)ethyl, 2-(N,N-diethylcarbamoyl)ethyl and 3-(N,N-dimethylcarbamoyl)propyl;

A preferred class of compounds of the present invention is that wherein:

A is 4-pyridyl, 4-pyrimidinyl or 4-pyridazinyl;

$B_1$ $_{to}$ $_4$ is forms a pyridinediyl, pyrimidinediyl or pyridazinediyl;

$X_1$ is CO, $SO_2$ or $CH_2$, ideally CO;

$T_1$ and $T_2$ are both N;

$L_1$ is ethylene or propylene;

$R_2$ and $R_3$ are joined to form an ethylene or propylene or methylenecarbonyl group;

wherein the heterocyclic ring formed by $T_1$, $T_2$, $L_1$, $R_2$ and $R_3$ is unsubstituted or is substituted;

$X_1$ is $SO_2$;

$B_5$ or $B_6$ is N:

n is 1 at the 5 position;

Y is halo, preferably bromo or chloro;

and pharmaceutically-acceptable salts thereof.

A particular compound of the invention is:

1-(5-chloroindol-2-ylsulphonyl)-4-[6-(4-pyridyl) nicotinoyl]piperazine; and 1-(5-bromoindol-2-ylsull,honyl)-4-[6-(4-pyridyl) nicotinoyl]piperazine.

Compounds of formula I, or pharmaceutically-acceptable salt thereof, may be prepared by any process known to be applicable to the preparation of related compounds. Such procedures are provided as a further feature of the invention and are illustrated by the following representative processes in which, unless otherwise stated A, $B_1$, $B_2$, $B_3$, $B_4$, $X_1$, $T_1$, $T_2$, $L_1$, $R_2$, $R_3$, $X_2$, $B_5$, $B_6$, Y and n have any of the meanings defined hereinbefore wherein any functional group, for example amino, alkylamino, carboxy or hydroxy, is optionally protected by a protecting group which may be removed when necessary.

Necessary starting materials may be obtained by standard procedures of organic chemistry.

According to another aspect, the present invention provides a process for preparing a compound of formula I or a pharmaceutically acceptable salt thereof. which comprises:

(a) For the production of compounds of the formula (I) wherein $T_1$ is N and $X_1$ is CO, by the reaction, conveniently in the presence of a suitable base, of an amine with an acid

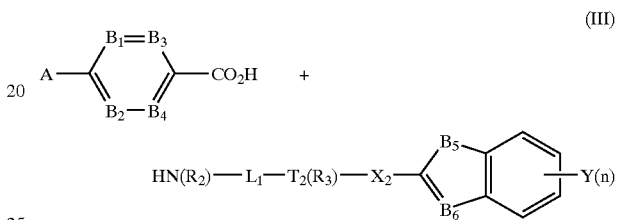

(III)

or with a reactive derivative of the acid.

A suitable reactive derivative of the acid is, for example, an acyl halide, an anhydride, an activated amide, an active ester, or the product of the reaction of the acid and a carbodiimide such as N,N'-dicyclohexylcarbodiimide or N-(3-dimethylaminopropyl)-N'-ethyl-carbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

(b) For the production of those compounds of formula I wherein $T_1$ is CH and $X_1$ is O by the reaction, conveniently in the presence of a suitable coupling agent;

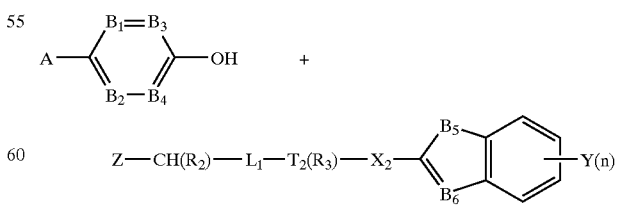

A suitable value for the displaceable group Z is, for example, a halogeno or sulphonyloxy group, for example a fluoro, chloro, bromo, mesyloxy or 4-tolylsulphonyloxy group.

A suitable reagent for the coupling reaction when Z is a halogeno or sulphonyloxy group is, for example, a suitable base, for example, an alkali or alkaline earth metal carbonate, hydroxide or hydride, for example sodium carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylfornamide, N,N-dimethylacetamide, dimethylsulphoxide, acetone, 1,2-dimethoxyethane or tetrahydrofuran, and at a temperature in the range, for example, −10° to 150° C., conveniently at or near ambient temperature.

An analogous procedure may be employed for the preparation of those compounds of the formula (I) wherein $T_1$ is CH and $X_1$ is a group of the formula S.

A suitable reagent for the coupling reaction of the alcohol, wherein Z is a hydroxy group, where the hydroxy group is converted in situ to a displaceable group as defined above, is, for example, the reagent obtained when said alcohol is reacted with a di-(1–4C)alkyl azodicarboxylate in the presence of a triarylphosphine or tri-(1–4C)alkylphosphine, for example with diethyl azodicarboxylate in the presence of triphenylphosphine or tributylphosphine. The reaction is preferably performed in a suitable inert solvent or diluent, for example acetone, 1,2-dimethoxyethane or tetrahydrofuran, and at a temperature in the range, for example, 10° to 80° C., conveniently at or near ambient temperature.

(c) For the production of those compounds of formula (I) wherein $T_1$ is N and $X_1$ is CH($R_4$), the reductive amination of a keto compound below:

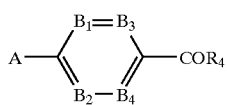

(VI)

with an amine as defined in (a) above.

A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride. The reaction is performed at a temperature in the range, for example, 10° to 80° C., conveniently at or near ambient temperature.

(d) By the reaction of:

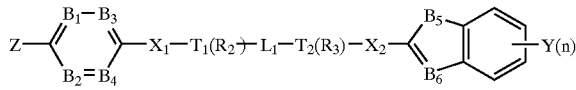

wherein Z is a displaceable group such as halo, with an activated derivative of heterocyclic ring A. Suitable activated derivatives include metalised derivatives, such as with zinc or tin, and borane derivatives. The activated derivative of heterocyclic ring A is reacted with the above compound to effect cross coupling where Z is a halo group, such as iodo, bromo or chloro and triflate. Suitably the reaction is catalysed by use of a transition state metal catalyst, such as palladium, e.g. tetrakis (triphenylphosphine) palladium(0).

Alternatively it is possible that ring A contains the displaceable group Z and the ring containing $B_1$ to $B_4$ is activated, as described above.

The reaction is not suitable for compounds which contain halo substituents on A, B, or $L_1$.

(e) By forming A ring on the above compound (d), wherein Z is a functional group capable of cyclisation. Suitable reagents and conditions are described in Bredereck H. Chem.Ber.; 96, 1505, (1963); Fuchigami, T., Bull. Chem. Soc. Jpn., 49, p3607, (1976); Huffman, K. R., J. Org. Chem., 28, p1812, (1963); Palusso, G., Gazz. Chim. Ital., 90, p1290, (1960) and Ainsworth C. J., Heterocycl. Chem., 3, p470, (1966). Processes suitable for synthesis of starting materials in such cyclisation reactions are described in Zhang M. Q. et.al; J. Heterocyclic. Chem.; 28, 673, (1991) and Kosugi, M. et al., Bull. Chem. Soc. Jpn., 60, 767–768 (1987).

(f) For the production of compounds wherein $T_2$ is N, by the reaction:

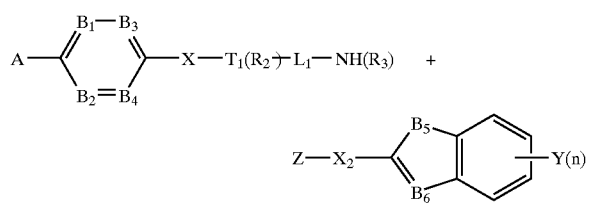

wherein Z is a displaceable group for example chloro, under conditions similar to those of process variant (a) above.

(g) For the production of compounds wherein $T_1$ is N and $X_1$ is SO or $SO_2$, by the reaction:

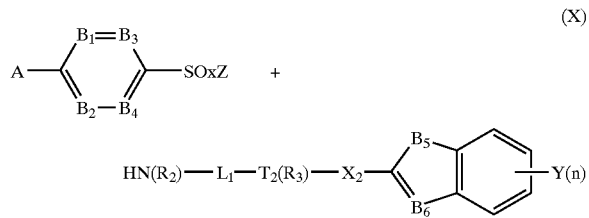

(X)

wherein x is one or two and Z is a displaceable group; under appropriate conventional coupling conditions, similar to those of process variant (a) above.

(h) By coupling the heteroaryl group to $T_2$ with methods analogous to those described in process variants (a), (c) and (f) for preparing the B—$X_1$—$T_1$— moiety may be employed.

(i) For the production of compounds of the formula (I) wherein $X_1$ is a group of the formula SO, $SO_2$, wherein the ring containing $B_1$ to $B_4$ bears a 1-oxothiomorpholino or 1,1-dioxothiomorpholino group or a substituent which contains a (1–4C)alkylsulphinyl, (1–4C)alkylsulphonyl, 1-oxothiomorpholino or 1,1-dioxothiomorpholino group, wherein $X_2$ is a group of the formula SO or $SO_2$. wherein Q bears a (1–4C)alkylsulphinyl, (1–4C)alkylsulphonyl. phenylsulphinyl, phenylsulphonyl, heteroarylsulphinyl or heteroarylsulphonyl group, the oxidation of the corresponding compound of the formula I wherein $X_1$, $X_2$, or both $X_1$ and $X_2$ is S.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as rnethylene chloride, chloroform, acetone, tetrahydrofuran or tert-butyl methyl ether and at a temperature, for example, at or near ambient temperature, that is in the range 15 to 35° C. Suitable reagents and conditions are described in, for example, Page G. O.; Synth. Commun. 23, (1993) 6, 765–769. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound. Those compounds of formula I which contain oxygen labile groups (such as A ring is pyridyl) are probably not suitable intermediates for this process step, unless oxidation of such groups is desired.

When a pharmaceutically-acceptable salt of a compound of the formula I is required, it may be obtained, for example, by reaction of said compound with a suitable acid or base using a conventional procedure.

When an optically active form of a compound of the formula I is required, it may be obtained, for example, by carrying out one of the aforesaid procedures using an optically active starting material or by resolution of a racemic form of said compound using a conventional procedure, for example by the formation of diastereomeric salts, use of chromatographic techniques, conversion using chirally specific enzymatic processes, or by additon of temporary extra chiral group to aid seperation.

As stated previously, the compounds of the formula I are inhibitors of the enzyme Factor Xa. The effects of this inhibition may be demonstrated using one or more of the standard procedures set out hereinafter:

a) Measurement of Factor Xa Inhibition

An in vitro assay system is carried out based on the method of Kettner et al., *J. Biol. Chem.*, 1990, 265, 18289–18297, whereby various concentrations of a test compound are dissolved in a pH7.5 buffer containing 0.5% of a polyethylene glycol (PEG 6000) and incubated at 37° C. with human Factor Xa (0.001 Units/ml., 0.3 ml) for 15 minutes. The chromogenic substrate S-2765 (KabiVitrum AB, 20 $\mu$M) is added and the mixture is incubated at 37° C. for 20 minutes whilst the absorbance at 405 nm is measured. The maximum reaction velocity (Vmax) is determined and compared with that of a control sample containing no test compound. Inhibitor potency is expressed as an $IC_{50}$ value.

b) Measurement of Thrombin Inhibition

The procedure of method a) is repeated except that human thrombin (0.005 Units/ml) and the chromogenic substrate S-2238 (KabiVitrum AB, 7 $\mu$M) are employed.

c) Measurement of Anticoagulant Activity

An in vitro assay whereby human, rat or rabbit venous blood is collected and added directly to a sodium citrate solution (3.2 g/100 ml, 9 parts blood to 1 part citrate solution). Blood plasma is prepared by centrifugation (1000 g. 15 minutes) and stored at 24° C. Conventional prothrombin time (PT) tests are carried out in the presence of various concentrations of a test compound and the concentration of test compound required to double the clotting time, hereinafter referred to as CT2, is determined. In the PT test, the test compound and blood plasma are incubated at 37° C. for 10 minutes. Tissue thromboplastin with calcium (Sigma Limited, Poole, England) is added and fibrin formation and the time required for a clot to form are determined.

d) An ex vivo Assay of Anticoagulant Activity

The test compound is administered intravenously or orally to a group of Alderley Park Wistar rats. At various times thereafter animals are anaesthetised, blood is collected and PT coagulation assays analogous to those described hereinbefore are conducted.

e) An in vivo Measurement of Antithrombotic Activity

Thrombus formation is induced using an analogous method to that described by Vogel et al., *Thromb. Research*, 1989, 54, 399–410. A group of Alderley Park Wistar rats is anaesthetised and surgery is performed to expose the vena cava. Collateral veins are ligated and two loose sutures are located, 0.7 cm apart, round the inferior vena cava. Test compound is administered intravenously or orally. At an appropriate time thereafter tissue thromboplastin (30 $\mu$l/kg) is administered via the jugular vein and, after 10 seconds, the two sutures are tightened to induce stasis within the ligated portion of vena cava. After 10 minutes the ligated tissue is excised anid the thrombus therein is isolated, blotted and weighed.

(f) Rat Disseminated Intravascular Coagulation in vivo Activity Test

Fasted male Alderley Park rats (300–450 g) are pre-dosed by oral gavage (5 mls/kg) with compound or vehicle (5% DMSO/PEG200) at various times before being anaesthetised with Intraval® (120 mg/kg i.p.). The left jugular vein and the right carotid artery are exposed and cannulated. A 1 mL blood sample is taken from the carotid canular into 3.2% trisodium citrate. 0.5 mL of the whole blood is then treated with EDTA and used for platelet count determination whilst the remainder is centrifuged (5 mins, 20000 g) and the resultant plasma frozen for subsequent drug level, fibrinogen or thrombin antithrombin (TAT) complex determinations. Recombinant human tissue factor (Dade Innovin Cat.B4212-50), reconstituted to the manufacturers specification, is infused (2 mL/kg/hr) into the venous canular for 60 minutes. Immediately after the infusion is stopped a 2 mL blood sample is taken and platelet count, drug level, plasma fibrinogen concentration and TAT complex are determined as before. Platelet counting is performed using at Coulter T540 blood analyser. Plasma fibrinogen and TAT levels are dertermining using a clotting assay (Sigma Cat.880-B) and TAT ELISA (Behring) respectively. The plasma concentration of the compound is bioassayed using human Factor Xa and a chromogenic substrate S2765 (Kabi), extrapolated from a standard curve (Fragmin) and expressed in Anti-Factor Xa units. The data is analysed as follows; tissue factor-induced reductions in platelet count are normalised with respect to pre-dose platelet count and drug activity expressed as a percent inhibition of tissue factorinduced thrombocytopenia when compared to vehicle treated animals. Compounds are active if there is statistically significant (p<0.05) inhibition of TF-induced thrombocytopenia.

Example had an $IC_{50}$ (Factor Xa) of 0.007 $\mu$M as measured in test a)

According to a further feature of the invention there is provided a pharmaceutical composition which comprises a heterocyclic derivative of the formula 1, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic derivative of the formula 1, or a pharrnaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided use of a heterocyclic derivative of the formula I, or a pharmaceutically-acceptable salt thereof, in the manufacture of a medicament for use in a method of treatment of the human or animal body by therapy.

The invention also includes the use of such an active ingredient in the production of a medicament for use in:

(i) producing a Factor Xa inhibitory effect;

(ii) producing an anticoagulant effect;

(iii) producing an antithrombotic effect;

(iv) treating a Factor Xa mediated disease or medical condition;

(v) treating a thrombosis mediated disease or medical condition;

(vi) treating coagulation disorders; and/or (vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula I will naturally vary according to the nature and severity of the medical condition, the age and sex of the animal or patient being treated and the route of administration; according to well known principles of medicine. As mentioned above, compounds of the formula I are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed, for example a dose for intravenous administration in the range, for exanple, 0.5 to 50 mg/kg body weight will generally be used. For preferred and especially preferred compounds of the invention, in general, lower doses will be employed, for example a daily dose in the range, for example, 0.5 to 10 mg/kg body weight.

Although the compounds of the formula I are primarily of value as therapeutic or prophylactic agents for use in warm-blooded animals including man, they are also useful whenever it is required to produce an anticoagulant effect, for example during the ex-vivo storage of whole blood or in the development of biological tests for compounds having nti-coagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known anti-hypertensive agent.

The invention will now be illustrated in the following Examples in which, unless otherwise stated:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gas such as argon;

(iii) the end-products of the formula I have satisfactory microanalyses and their structures were confirmed by nuclear magnetic resonance (NMR) and mass spectral techniques. Chemical shift values were measured on the delta scale; the following abbreviations have been used: s, singlet; d, doublet; t, triplet; q, quartet; m, multiplet;

(iv) intermediates were not generally fully characterised and purity was assessed by thin layer chromatographic, infra-red (IR) or NMR analysis; and (v) melting points were determined using a Mettler SP62 automatic melting point apparatus or an oil oath apparatus; melting points for the end-products of the formula I were generally determined after crystallisation from a conventional organic solvent such as ethanol, methanol, acetone, ether or hexane, alone or in admixture.

EXAMPLE 1

1-(5-Chloroindol-2-ylsulphonyl)-4-[6-(4-pyridyl) nicotinoyl]piperazine

A stirred suspension of 6-(4-pyridyl)nicotinic acid (400 mg, 2 mmol) in dimethylformamide, DMF, (10 ml) was treated with 1-(5-chloroindol-2-ylsulphonyl)piperazine (600 mg, 2 mmol, 1 mol eq.) and 1-(3-dimethylaminopropyl)-3-ethylcarbodi-imide hydrochloride (EDAC, 460 mg, 2.4 mmol, 1.2 mol eq.). After stirring overnight the solvent was removed in vacuo and the residue chromatographed (Isolute 20 g silica cartridge, eluting with dichloromethane containing 2.5%–5% v/v of methanol) to yield 1-(5-chloroindol-2-ylsulphonyl)-4-[6-(4-pyridyl)nicotinoyl]piperazine as a colourless foam (680 mg). This was dissolved in dichloromethane/methanol mixture (40 ml of 1:1) and treated with a saturated solution of HCI in methanol until acid to indicator paper (slight excess). The resulting solution of hydrochloride salt was evaporated to dryness and the residue boiled in 2-propanol (100 ml, incomplete solution).

Filtration and cooling gave 1-(5-chloroindol-2-ylsulphonyl)-4-[6-(4-pyridyl)nicotinoyl]piperazine hydrochloride as a colourless solid, (220 mg), $^1$H NMR (d$_6$-DMSO) 3.0–3.3 (broad d, 4H), 3.6–4.0 (broad d, 4H), 7.05 (s, 1H), 7.35 (dd, 1H), 7.5 (d, 1H), 7.8 (d, 1H), 8.1 (dd, 1H), 8.35 (d, 1H), 8.5 (m, 2H), 8.8 (d, 1H), 8.95 (d, 2H), 12.4 (s, 1H), signals were also present due to 2-propanol (0.5 mol equiv.); MS (M+H)$^+$ 481/483; mp 186–190° C. (not sharp).

The requisite 64-pyridyl)nicotinic acid starting material was prepared as follows:

A solution of 1-[6-(4-pyridyl)-3-pyridyl]-4-(tert.-butyloxycarboryl)-piperazine (3.7 g, 10 mnuol) and potassium carbonate (6.9 g, 50 mmol) in methanol/wate, (90 ml of a 2:1 mixture) (30 ml) was heated vat reflux for 7 hrs. It was then cooled and neutralised with dilute HCl (50 ml of 2M), and some of the solvent removed in vacuo. More water was added and the resultant slurry left to stand for 2 hrs. Filtration, washing with water and drying gave the above starting material (870 mg) which was used without further purification, $^1$H NMR (d$_6$-DMSO), 8.1 (d, 2H), 8.25 (d, 1H), 8.45 (dd, 1H), 8.75 (d, 2H), 9.2 (d, 1H), MS (M+H)$^+$201, (M−H)$^-$199.

1-[6-(4-Pyridyl)-3-pyridyl]-4-(tert.-butyloxycarbonyl)-piperazine was prepared as shown in Example 1 of PCT/GB98/02210.

1-(5-Chloroindol-2-ylsulphonyl)piperazine was prepared as shown in Example 3 of GB9809351.1.

EXAMPLE 2

1-(5-Bromoindol-2-ylsulphonyl)-4-[6-(4-pyridyl)nicotinoyl]piperazine

By an exactly analogous method to that in Example 1, starting from 6-(4-pyridyl)nicotinic acid (400 mg, 2 mmol) and 1-(5-bromoindol-2-ylsulphonyl)piperazine (700 mg, 2 mmol, 1 mol eq.), was prepared 1-(5-bromoindol-2-ylsulphonyl)-4-[6-(4-pyridyl)nicotinoyl]piperazine free base, as a colourless solid, (540 mg), $^1$H NMR (d$_6$-DMSO) 3.0–3.3 (broad d, 4H), 3.4–3.9 (broad d, 4H), 7.0 (s, 1H), 7.45 (s, 2H), 7.95 (s, 1H), 8.0 (d, 1H), 8.1 (dd, 2H), 8.15 (d, 1H), 8.75 (m, 3H), 12.4 (s, 1H), signals were also present due to DMF (1 mol equiv.); MS (M+H)$^+$526/528.

The requisite 1-(5-bromoindol-2-ylsulphonyl)piperazine starting material was prepared in a manner analogous to that for the corresponding 5-chloro compound.

What is claimed is:
1. A compound of the formula I

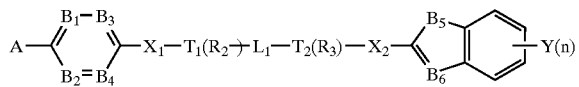

wherein:
A is a 5- or 6-membered monocyclic aromatic ring containing 1, 2 or 3 ring heteroatoms selected from oxygen, nitrogen and sulphur atoms, optionally substituted by one, two or three atoms or groups selected from halo, trifluoromethyl, cyano, amino, oxo, hydroxy, nitro, (1–4C)alkyl, (1–4C)alkoxy, (1–4C)alkylamino or di-(1–4C)alkylamino;

$B_1$, $B_2$, $B_3$ and $B_4$ are independently CH or a nitrogen atom, with the proviso that at least one of $B_1$, $B_2$, $B_3$ and $B_4$ is nitrogen; wherein the ring formed from $B_1$, $B_2$, $B_3$ and $B_4$ may optionally be substituted by one or two substituents selected from hydroxy, carboxy, (1–4C)alkoxycarbonyl or one of the following;

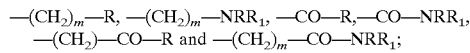

wherein m is 1 or 2;
R and $R_1$ are independently selected from hydrogen, (1–4C)alkyl, (2–4C)alkenyl, (2–4C)alkynyl, hydroxy(1–4C)alkyl, carboxy(1–4C)alkyl and (1–4C)alkoxycarbonyl-(1–4C)alkyl or R and $R_1$ may together form a 5- or 6-membered optionally substituted heterocyclic ring which may include in addition to the nitrogen atom to which R and $R_1$ are attached 1 or 2 additional heteroatoms selected from nitrogen, oxygen and sulphur;

$X_1$ is CO, SO$_2$, or CH$_2$;

$R_2$ and $R_3$ are ioined to form an ethylene group to form, together with $T_1$, $T_2$ and $L_1$ a piperazine ring, which is unsubstituted or is substituted by one or two substituents independently selected from hydroxy, oxo, carboxy, (1–4C)alkoxycarbonyl or one of the following;

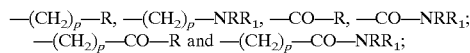

wherein n is 1 or 2;
R and $R_1$ are independently as defined above,

Y is selected from hydrogen, halo, trifluromethyl, trifluoromethoxy, cyano, hydroxy, amino, nitro, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl and N,N-di-(1–4C)alkylcarbamoyl-(1–4C)alkyl;

n is 1 or 2; and
one of $B_5$ and $B_6$ is N and the other is CH;
or a pharmaceutically acceptable salt thereof.

2. A compound of the formula I as claimed in claim 1 wherein A is a pyridyl, pyrimidinyl or pyridazinyl ring.

3. A compound of the formula I as claimed in claim 2 wherein A is 4-pyridyl, 2-pyridyl, 4-pyridazinyl, 3-pyrimidinyl, 4-pyrimidinyl or 3-pyridyl.

4. A compound of the formula I as claimed in claim 1 wherein A is unsubstituted or is substituted by one,m two or three atoms or groups selected from fluoro, chloro or bromo, trifluoromethyl, cyano, amino, oxo, hydroxy, nitro, methyl or ethyl, methoxy or ethoxy, methylamino, ethylamino, dimethylamino and diethylamino.

5. A compound of the formula I as claimed in claim 1, wherein the ring formed by $B_1$, $B_2$, $B_3$ and $B_4$ is a pyridinediyl, wherein $B_1$, or $B_3$ is a nitrogen atom, pyrimidinediyl, wherein $B_1$ and $B_2$ or $B_3$ and $B_4$ are nitrogen atoms or a ring, wherein $B_1$, $B_3$, $B_4$ or $B_1$, $B_2$, $B_3$ are nitrogen atoms.

6. A compound of the formula I as claimed in claim 1, wherein the ring containing $B_1$, $B_2$, $B_3$ and $B_4$ is unsubstituted.

7. A compound of the formula I as claimed in claim 1, wherein the heterocylcic ring formed by R and $R_1$ is selected from pyrrolidin-1-yl, imidazolin-1-yl, piperidin-1yl, piperazin-1-yl, 4-morpholino and 4-thiomorpholino.

8. A compound of the formula I as claimed in claim 1, wherein the heterocyclic ring formed by R and $R_1$ is unsubstituted or the ring formed by R and $R_1$ is substituted by 1 or 2 substituents selected from oxo, hydroxy and carboxy.

9. A compound of the formula I as claimed in claim 1, wherein Y is selected from hydrogen, halo, trifluromethyl, trifluoromethoxy, cyano, hydroxy, amino, nitro, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino and (1–4C)alkoxycarbonyl.

10. A compound of formula (I) as defined in claim 1 wherein

A is 4-pyridyl, 4-pyrimidinyl or 4-pyridazinyl;

the ring containing $B_{1\ to\ 4}$ forms a pyridinediyl, pyrimidinediyl or pyridazinediyl ring;

$X_1$ is CO;

n is 1 at the 5 position; and

Y is halo or a pharmaceutically-acceptable salt thereof.

11. A compound according to claim 10 wherein Y is chloro or bromo.

12. A pharmaceutical composition which comprises a compound of the formula I, as defined in any one of claims 1 to 8 and 9 or a pharmaceutically-acceptable salt thereof, in association with a pharmaceutically-acceptable diluent or carrier.

13. A method for producing a Factor Xa inhibitory effect, said method comprising administering to a warm-blooded animal in need thereof an inhibition-effective amount of a compound of formula I as defined in any one of claims 1 to 8 and 9 or a pharmaceutically-acceptable salt thereof.

* * * * *